(12) United States Patent
Mochizuki et al.

(10) Patent No.: US 6,994,824 B2
(45) Date of Patent: Feb. 7, 2006

(54) ARTIFICIAL CARDIOPULMONARY CIRCUIT SYSTEM

(75) Inventors: Akira Mochizuki, Yamanashi (JP); Kenichi Shimura, Yamanashi (JP); Takao Anzai, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 729 days.

(21) Appl. No.: 10/180,321

(22) Filed: Jun. 27, 2002

(65) Prior Publication Data

US 2003/0028073 A1    Feb. 6, 2003

(30) Foreign Application Priority Data

Jun. 28, 2001  (JP)  ............................. 2001-195980

(51) Int. Cl.
*A61M 1/14*   (2006.01)
*A61M 37/00*  (2006.01)
*A61M 1/34*   (2006.01)
*B01D 39/00*  (2006.01)

(52) U.S. Cl. .................. 422/48; 604/6.14; 210/500.35; 210/500.23; 210/490

(58) Field of Classification Search .............. 422/45, 422/48, 49; 604/6.13, 6.01, 6.14; 210/500.35, 210/500.23, 490; 261/DIG. 28; 128/DIG. 23
See application file for complete search history.

(56) References Cited

U.S. PATENT DOCUMENTS 3,692,648 A * 9/1972 Matloff et al. ............ 205/633
4,923,679 A * 5/1990 Fukasawa et al. ......... 422/48
6,495,101 B1 * 12/2002 Yokoyama et al. ........ 422/48

FOREIGN PATENT DOCUMENTS

EP       0 908 191 A1 *  4/1999
JP       04-152952 A      5/1992
JP       07-313854 A     12/1995
JP       11-114056 A      4/1999

OTHER PUBLICATIONS

T. Matsuda et al., "Complement Activaton on Polymer Surfaces and Its Effector Function to Immunocompetent Cells", *Jpn. J. Artificial Organs*, 16(2), pp. 1045-1050 (1987).

* cited by examiner

Primary Examiner—Sharon Kennedy
(74) Attorney, Agent, or Firm—Buchanan Ingersoll PC

(57) ABSTRACT

To provide an artificial cardiopulmonary circuit system having high heat resistance and excellent blood compatibility. The artificial cardiopulmonary circuit system includes a hollow fiber membrane oxygenator including a plurality of porous hollow fiber membranes for gas exchange having a blood contact part that contacts blood on one side thereof and a gas contact part that contacts a gas on the other side thereof, and a housing that contains the hollow fiber membranes therein. At least a portion of the blood contact part of the hollow fiber membrane oxygenator is coated with a polymer comprising a repeating unit represented by the following general formula (1) as a main structural component and having a viscosity at 65° C. of 5,000 poise (500 Pa·s)

[Chemical Formula 4]

$$-CH_2-CR^1- \atop | \atop COO-R^2-O-R^3 \quad (1)$$

(Wherein $R^1$ is hydrogen or a methyl group, $R^2$ is an alkylene group having 1 to 4 carbon atoms, and $R^3$ is an alkyl group having 1 to 4 carbon atoms).

8 Claims, 1 Drawing Sheet

ARTIFICIAL CARDIOPULMONARY CIRCUIT SYSTEM

BACKGROUND OF THE INVENTION

1. Field of the Invention

The present invention relates to an artificial cardiopulmonary circuit system excellent in organism compatibilities. More particularly, the present invention relates to an artificial cardiopulmonary circuit system having a blood contact part coated with a polyalkoxyalkyl (meth)acrylate material being excellent in blood compatibility.

2. Description of the Related Art

In recent years, medical instruments using polymer materials have been developed and used in a variety of quarters. Examples thereof include artificial kidneys, oxygenators, plasma separation membranes, catheters, artificial vessels, artificial joints, artificial skins and so forth. Artificial polymers when introduced into living organisms become foreign substances to the organisms and cause various biophylaxis reactions, so that events that are undesirable to the organisms occur. Accordingly, currently development of materials that do not cause biophylaxis reactions, i.e., those are excellent in organism compatibilities or blood compatibilities is demanded. It is known that materials having micro phase separated structures comprised by a hydrophilic phase and a hydrophobic phase are excellent in blood compatibilities, in particular platelet compatibilities. However, to attain this, phase separation of a specific size must be developed and the conditions that control this structure are limited within a narrow range, so that their use is limited. It is also known that the platelet compatibility can be developed by forming a hydrogel made of polyethylene glycol or the like on a surface of the material. However, the compatibility lasts only for a short period of time and it is difficult to develop a long-lasting compatibility. On the other hand, platelets considerably adhere to a surface of hydrophobic materials such as polypropylene and polyethylene terephthalate to cause activation thereof.

On the other hand, in the case of the compatibility to a complement system in the blood compatibility, it is known that the activity of complement is remarkable on cellulose and ethylene/vinyl alcohol copolymer and that the hydroxyl groups present in the polymers constitute the cause of activation. On the contrary, hydrophobic materials including polypropylene are known to have less complement activity (Jinko Zoki (Artificial Organ) 16 (2), pp 1045–1050 (1987)).

Polyalkoxyalkyl (meth)acrylate is disclosed in JP 4-152952 A as a material having platelet compatibility, anti-complement activity, easy controllability of surface and so forth in good balance and placed in practical use as a coating material.

However, this material is a noncrystalline polymer that has a glass transition temperature of 0° C. or less and is in a state of a hard candy and does not almost flow at room temperature but once temperature is increased, naturally it develops flowability. Therefore, for medical instruments coated with this material, the flow characteristics of the material become a big concern. That is, the material receives a great influence when it undergoes a production process to which heat is applied for evaporation of a coating solvent, gas sterilization and the like. Furthermore, during a transporting process, when left to stand in a car in summer seasons, the material is exposed to a high temperature environment, which possibly becomes a big problem in stabilization of the quality and performance of the material. Specifically, in a case where polyalkoxyalkyl methacrylate is adapted to an artificial cardiopulmonary circuit system including a hollow fiber membrane oxygenator, when the temperature is increased because of the above-mentioned cause, there is the possibility that the flowability of the polymer increases and the polymer penetrates into micro pores of the membrane to decrease the gas exchangeability of the membrane.

SUMMARY OF THE INVENTION

An object of the present invention is to provide an artificial cardiopulmonary circuit system having organism compatibilities with high stability comprising a polyalkoxyalkyl (meth)acrylate having a viscosity of at least a specific value even if it is placed in high temperature atmosphere as a coating material at a blood contact part thereof. Specifically, it is an object of the present invention to provide an artificial cardiopulmonary circuit system including a coating material including a polyalkoxyalkyl (meth)acrylate having a melt viscosity at 65° C. of 5,000 poises (500 Pa·s) or more.

The present invention relates to an artificial cardiopulmonary circuit system including a hollow fiber membrane oxygenator including: a plurality of porous hollow fiber membranes for gas exchange wherein has a blood contact part that contacts blood on one side thereof and a gas contact part that contacts a gas on the other side thereof; and a housing that contains the hollow fiber membranes therein, characterized in that at least a portion of the blood contact part of the hollow fiber membrane oxygenator is coated with a polymer comprising a repeating unit represented by the following general formula (1) as a main structural component and having a viscosity at 65° C. of 5,000 poise (500 Pa·s)

[Chemical Formula 1]

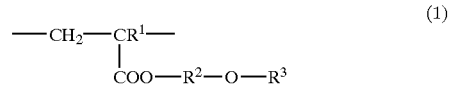

(Wherein $R^1$ is hydrogen or a methyl group, $R^2$ is an alkylene group having 1 to 4 carbon atoms, and $R^3$ is an alkyl group having 1 to 4 carbon atoms).

The present invention relates to the above-mentioned artificial cardiopulmonary circuit system, in which the polymer is polymethoxyethyl acrylate (i.e., $R^1$ is hydrogen, $R^2$ is an ethylene group, and $R^3$ is a methyl group).

The present invention relates to the above-mentioned artificial cardiopulmonary circuit system, in which the polymer has a viscosity of 7,800 poises (780 Pa·s) or more.

The present invention relates to the above-mentioned artificial cardiopulmonary circuit system, in which the polymer has a covering amount of 0.02 to 0.5 g/m².

The artificial cardiopulmonary circuit system of the present invention is an extracorporeal blood circulation circuit system for removing carbon dioxide in blood and adding oxygen into blood in place of the lung of an organism at the time of open heart surgery or the like and may include as parts constituting the artificial cardiopulmonary circuit system a hollow fiber membrane oxygenator and in addition thereto an arterial filter, a bubble trap, a reservoir, a cardioplegia, a centrifugal pump, a cannula, and tubes or connectors connecting them.

Specifically, the hollow fiber membrane oxygenator used in the present invention is provided with a blood flow passage having a blood flow inlet port and a blood flow outlet port on the side of the blood contact part through a porous membrane being a plurality of porous hollow fiber membrane with a gas flow passage having a gas flow inlet port and a gas flow outlet port on the side of a gas contact part. The hollow fiber membrane oxygenator uses a number of hollow fibers made of a hydrophobic material such as polypropylene having a myriad of micro pores with a micro pore diameter of from several tens Angstroms to 0.1 μm for increasing the gas exchangeability (cf., JP 7-313854 A); the gas flows inside the hollow fibers as laminar flows and blood flows in the interstice between an outer cylinder and the hollow fibers. The hollow fiber membrane may be formed from synthetic polymers such as polyethylenes, polystyrenes, polypropylenes, polysulfones, polymethyl methacrylates, and polytetrafluoroethylenes as materials.

In the artificial cardiopulmonic circuit system of the present invention, at least a portion of the blood contact part of the hollow fiber membrane oxygenator is coated with a specific polymer and it is preferred that also the blood contact parts of constituent parts other than the hollow fiber membrane oxygenator are coated with the specific polymer.

DETAILED DESCRIPTION OF THE INVENTION

Figure 1:
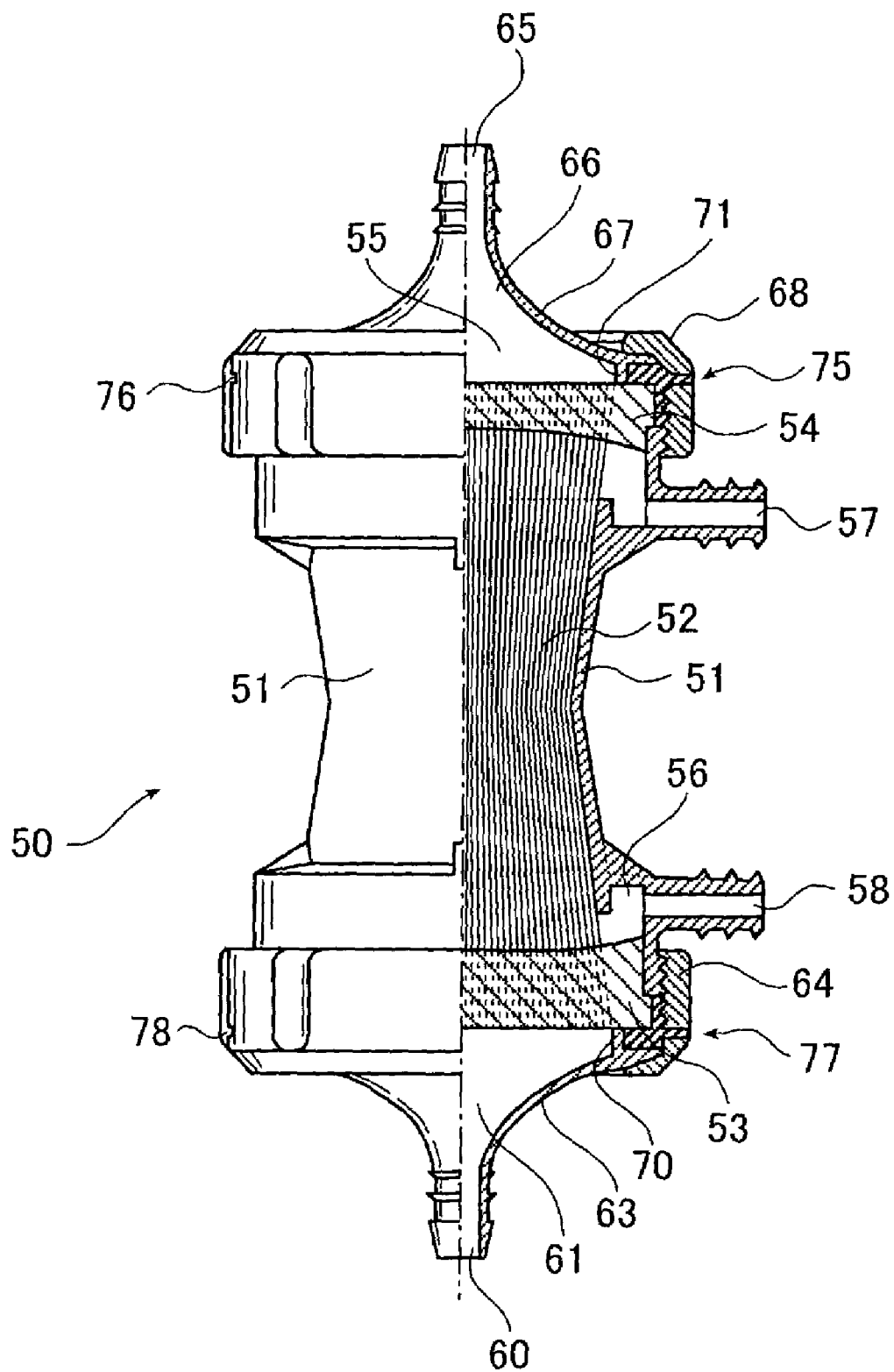
FIG. 1 is a partial cross section showing one example of hollow fiber membrane oxygenator used in the artificial cardiopulmonary circuit system of the present invention.

Hereinafter, one preferred example of the hollow fiber membrane oxygenator used in the present invention will be described in detail by referring to FIG. 1. However, the present invention should not be considered as being limited thereto.

FIG. 1 shows a hollow fiber membrane oxygenator according to one embodiment of the present invention in an assembled state. An artificial fiber membrane oxygenator 50 includes a cylindrical housing 51 and a plurality of porous hollow fiber membranes 52. The hollow fiber membranes 52 are contained in and extending throughout the housing 51 and serving as gas exchange membranes. The hollow fiber membranes 52 are in the form of cylinders that have each a cavity inside and outer and inner surfaces, with the membrane walls being provided with a number of micro pores forming gas flow passages communicating the inside and outside of the hollow fiber membranes. The both ends of each hollow fiber membrane 52 are liquid tightly fixed to the housing 51 by bulkheads 53 and 54 without each opening of hollow fiber which constitute the hollow fiber membrane 52 being occluded. The inside of the housing 51 is divided into a blood flow passage 56, which is a first material transport chamber formed by the outer surface of the hollow fiber membranes, the inner wall of the housing 51, and bulkheads 53 and 54; and a gas flow passage 55, which is a second material transport chamber formed inside the hollow fiber membranes (hollow fiber).

The housing 51 is provided in the vicinity of one end thereof with a gas flow inlet port 60 for a gas containing oxygen and in the vicinity of the other end thereof with a gas flow outlet port 65. Therefore, in the membrane oxygenator 50 shown in FIG. 1, the hollow fiber membranes 52 through which gas exchange is carried out between blood and gas are membrane walls having micro pores, with a blood contact part on one side thereof that contact blood being constituted by the outer surface of the hollow fiber membranes 52 and a gas contact portion on the other side thereof being constituted by the inner surface of the hollow fiber membranes 52.

The hollow fiber membrane oxygenator used in the present invention has formed a blood flow passage 56 provided with a blood flow inlet port 57 and a blood flow outlet port 58 on the side of the blood contact part through the hollow fiber membrane 52, and a gas flow passage 55 provided with a gas flow inlet port 60 and a gas flow outlet port 65 on the side of the gas contact part. Furthermore, onto the outside of the bulkhead 53 is fixed a flow passage forming member 63 having the gas flow inlet port 60 and an annular convex portion 61 through a threaded ring 64. Also, on the outside of the bulkhead 54 is fixed a flow passage forming member 67 having a gas flow outlet port 65 and an annular convex portion 66 through a threaded ring 68. Convex portions 70 and 71 of the flow passage forming members 63 and 67 abut the bulkheads 53 and 54, respectively. To the respective outer peripheries of the convex portions 70 and 71 are filled a sealant through at least each one of two holes 75 and 76, and 77 and 78, respectively provided in the threaded rings 64 and 68 to liquid tightly fix the passage forming members 63 and 67 to the bulkheads 53 and 54, respectively. In the above-mentioned hollow fiber membrane oxygenator used in the present invention, at least a portion of the blood contact part of the hollow fiber membranes 52, that is, at least the outer surface of the hollow fiber membrane 52 are coated with the specific polymer described hereinafter.

The whole or a part of blood contact part of the porous membrane may be coated. An average covering amount on the blood contact part is preferably 0.02 to 0.5 g/m$^2$, more preferably 0.05 to 0.2 g/m$^2$. With the average covering amount being within this range, an artificial cardiopulmonary circuit system excellent in blood compatibility and heat stability can be obtained.

In the present invention, the blood contact part of the hollow fiber membrane is coated with a synthetic polymer comprising alkoxyalkyl (meth)acrylate of the general formula (1), a repeating unit, as a constituent unit.

[Chemical Formula 2]

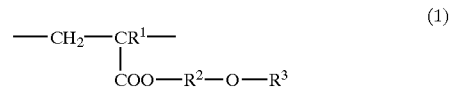

wherein, R$^3$O— is an alkylalkoxy group having 1 to 4 carbon atoms such as methoxy group, ethoxy group, propoxy group and butoxy group; —R$^2$— is an alkylene group having 1 to 4 carbon atoms such as methylene group, ethylene group, propylene group and butylene group; and R$^1$ is hydrogen or methyl group. Among these combinations, methoxyethyl acrylate is particularly desirable having a combination in which R$^3$O— is methoxy group, —R$^2$— is ethylene group and R$^1$ is H, from the viewpoint of blood compatibility and cost effectiveness.

The above-mentioned polymer has a viscosity at 65° C. of 5,000 poises (500 Pa·s) or more, preferably 7,800 poises (780 Pa·s) or more, more preferably 15,000 poises (1,500 Pa·s) to 20,000 poises (2,000 Pa·s). With the viscosity of the polymer being within this range, the heat stability required of oxygenators can be obtained, that is, the oxygenators have the effect of preventing the occlusion of the micro pores in the porous membrane due to self flow of the alkoxyalkyl (meth)acrylate.

Generally, the alkoxyalkyl (meth)acrylate polymers have glass transition temperatures at or below room temperature and hence they are in the form of candy at room temperature and exhibit flowability depending on the molecular weight thereof. After coated on a porous article such as an oxygenator membrane, the polymer may be exposed to temperatures as high as about 60 to about 70° C. in the process of distilling off solvents or sterilization or in the process of distribution. For this reason, the coated polymer will have a decreased viscosity to increase flowability. On this occasion, if the viscosity is decreased too much, the polymer may be undesirably absorbed in the micro pores due to capillarity. This means occlusion of the micro pores, indicating the possibility of a decrease in gas exchangeability. The decrease in gas exchange performance will not cause a serious clinical problem so far as the decrease is up to about 15% but if the decrease exceeds about 15%, there is the possibility that the performance of the membrane will be decreased. In specifically, for example, gas exchange performance can be measured by the gas flux method described below in example 1.

The viscosity of a polymer is greatly influenced by the molecular weight distribution and hence a desirable molecular weight of the polymer is not uniquely defined. However, in the case of a polymer having a narrow molecular weight range wherein the ratio (Mw/Mn) dividing weight average molecular weight (Mw) by number average molecular weight (Mn) as low as about 1 to about 1.5, weight average molecular weight of the polymer (Mw) is preferably about 40,000 or more, and more preferably about 60,000 or more as a guideline. On the other hand, in the case where the polymer has a broad molecular weight range as broad as the ratio (Mw/Mn) of about 2.0 to about 3.0, a guideline of Mw is about 200,000 or more. The viscosity as used herein means a viscosity as measured by using a rotary viscometer. In the present study, the viscosity was measured by using an E type viscometer Visconic EHD type manufactured by Tokyo Keiki Co., Ltd. having a rotary disc of a conical shape with a diameter of 15.4 mm at 0.5 rpm at a temperature of 65° C.

The polyalkoxyalkyl (meth)acrylate that can be used in the present invention may be obtained by a known polymerization/purification method. That is, it can be synthesized by radial polymerization using a peroxide or an azo compound as an initiator, radiation radical polymerization using radiation such as gamma ray, or anion polymerization using an organometallic compound as an initiator. Among them, monodisperse polymer obtained by living anion polymerization can provide a polymer having blood compatibility in the simplest manner. When the above-mentioned polymer is synthesized by radical polymerization, the ratio (Mw/Mn) becomes large value, therefore the range of the molecular weight distribution becomes broad and plasticizing effect of the low molecular region works so that it becomes necessary to make the average molecular weight extremely large in order to increase the viscosity to a high level or remove polymers in the low molecular weight region by fractional precipitation. For this high polymerization, the purification of monomers and polymerization solvents in high precision and the fractional precipitation needs a large amount of organic solvents/organic non-solvents. Both ways unavoidably involve an increase in costs. From these, it follows that in the blood compatible alkoxyalkyl (meth)acrylate material for use in the present invention, it is preferred that the polymer synthesized by an anion polymerization method is used in consideration of ease of synthesis and ease of purification process. The polymer used in the present invention has the ratio (Mw/Mn) in the range of 1.0 to 1.5 and more preferably 1.0 to 1.2.

The blood compatible material used in the present invention is usually a homopolymers including only a repeating unit of the formula (1) described above. However, to improve the physical properties of the thus obtained polymer, copolymers or mixtures of other monomer units may also be used. Examples of other monomers include unsaturated hydrocarbons such as styrene, butadiene and isoprene; acrylate monomers such as (meth)acrylic acid esters, e.g., methyl (meth)acrylate, ethyl (meth)acrylate, butyl (meth)acrylate, etc.; acrylamide monomers such as acrylamide, N,N-dimethylacrylamide, and morpholineacrylamide and the like. The types of copolymer may be any of random polymerization, block copolymerization, and graft copolymerization and so forth without hindrance. It should be noted that the use amounts of other monomers may be in ranges where the blood compatibility and heat resistance of the polymer mainly constituted from the repeating unit of the formula (1) used in the present invention are not harmed. In specifically, other monomers can be used in 40 mol % or less of whole polymer, more preferably 10 mol % or less, still more preferably 5 mol % or less.

EXAMPLES

Hereinafter, the present invention will be described in detail by examples. However, the present invention should not be considered to be limited thereto. It should be noted that since it is impossible to reproduce all the thermal hystereses that could be received by actual hollow fiber membrane oxygenators, substitute experiments were carried out. That is, the hollow fiber module shown in FIG. 1 as one example was placed in an air oven at 60° C. for 1 hour and a ratio of gas flux was obtained by measurement of gas flow rates before and after the heat treatment. The heat resistance of the hollow fiber module was evaluated by ranking those samples in which the ratio of gas flux after the heat treatment is 85% or higher as compared with non-heated samples as passing the test. Also, the oxygenator module of example 1–5 described below was incorporated into an external circulation circuit system. In the system, blood perfusion was done at 37° C. of blood temperature, 1 L/min of flow rate, for 4 hours. The change rate of platelet in blood was 15% or less after 240 min (the measuring method is described JP 11-114056 A).

Example 1

To a solution of 10 g of methoxyethyl acrylate in 90 ml of toluene was added azobisisobutyronitrile (AIBN) in an amount equivalent to 0.3 to 0.7 wt % based on the monomer and the mixture was heated at 70° C. overnight under nitrogen atmosphere to perform the synthesis of polymethoxyethyl acrylate (hereinafter abbreviated in some cases as "PMEA") by a radical polymerization method. The thus obtained polymer was reprecipitated from a solution in mixed solvent of hexane/diethyl ether to obtain PMEA. The viscosity of the PMEA thus obtained was measured by using an E type viscometer Visconic EHD type manufactured by Tokyo Keiki Co., Ltd. having a rotary disc of a conical shape with a diameter of 15.4 mm at 0.5 rpm at a temperature of 65° C. and the results are shown in Table 1. Furthermore, the thus obtained PMEA was coated on the outer surface of the hollow fiber membranes shown illustrated in FIG. 1. That is, the PMEA was dissolved in a mixed solvent of water:methanol:etanol of 6:1:3 to prepare a polymer solution having a concentration of 0.5 wt %. The solution was flown to the blood flowing side of an oxygenator module having a membrane surface area of 1.8 m² and comprised of porous polypropylene hollow fiber membranes having an inner diameter of 195 μm, an outer diameter of 295 μm and a porosity of 35%, to thereby coat the entire blood contact part of the oxygenator with the PMEA. After distilling off the solvent, the gas flux of the oxygenator module was measured by flowing N₂ gas. Then, the oxygenator module was placed in an air oven at 60° C. for 1 hour to perform heat treatment and then the gas flux thereof was measured similarly. The results of measurement of gas flux retention (%) are shown in Table 1. It should be noted that the PMEA covering amount of the blood contact part as measured by a solvent extraction method using methanol was 0.17 g/m² in average.

Example 2

A solution of 10 g of methoxyethyl acrylate in 90 ml of toluene was cooled to −60° C. Here, butyllithium, a polymerization catalyst, was added and the mixture was stirred for 10 hours under nitrogen atmosphere to perform polymerization. To deactivate living terminals of the polymer, methanol was added to stop the polymerization reaction. Thereafter, the toluene solution was washed with diluted hydrochloric acid to remove metal derived from the catalyst and then washed with distilled water. Then, this was reprecipitated in hexane to obtain anion polymerized PMEA. The viscosity and gas flux retention (%) of the thus obtained PMEA, and PMEA covering amount of the blood contact part were measured in the same manner as in Example 1. The results obtained are shown in Table 1.

Examples 3 to 5

Radical polymerization or anion polymerization conditions (polymerization initiator, polymerization time, reaction temperature, and reaction solvent) were changed to obtain various PMEAs. The viscosity, gas flux retention (%), and PMEA covering amount of the blood contact part of were measured with respect to each of the thus obtained PMEAs in the same manner as in Examples 1 and 2. The results obtained are shown in Table 1.

Comparative Examples 1 and 2

Polymerization was performed by the same radical polymerization process as in Example 1 except that the polymerization initiator, polymerization time, reaction temperature, and reaction solvent were varied to obtain PMEAs having viscosities of 4,200 poises (420 Pa·s) and 2,300 poises (230 Pa·s), respectively. The viscosity and gas flux retention (%) of each of the thus obtained PMEAs were measured in the same manner as in Examples 1 to 5 and the results obtained are shown in Table 1.

| | Viscosity of PMEA | Polymerization method | Gas flux retention (%) | Covering amount (g/m²) |
|---|---|---|---|---|
| Experimental Example | Noncoated | — | 100 | 0 |
| Example 1 | 1800 | Radical polymerization | 98 | 0.17 |
| Example 2 | 1600 | Anion polymerization | 98 | 0.17 |
| Example 3 | 1200 | Radical polymerization | 99 | 0.16 |
| Example 4 | 780 | Radical polymerization | 99 | 0.15 |
| Example 5 | 570 | Anion polymerization | 87 | 0.15 |
| Comparative Examples 1 | 420 | Radical polymerization | 75 | 0.15 |
| Comparative Examples 2 | 230 | Radical polymerization | 65 | 0.14 |

Conventionally, in the case that the contact part of the artificial cardiopulmonary circuit system is coated with a blood compatible material, it sometimes caused the problem of a decrease in gas exchange rate due to penetration of the coating solution into the inside of micro pores to cause occlusion of the micro pores. In contrast, the artificial cardiopulmonary circuit system of the present invention, which has the blood contact part coated with a polyalkoxy (meth)acrylate polymer being excellent in blood compatibility and having a specific viscosity, can retain its uniformly coated state even when exposed to high temperature environments during or after the production process, and therefore has high organism compatibilities.

What is claimed is:

1. An artificial cardiopulmonary circuit system comprising a hollow fiber membrane oxygenator comprising: a plurality of porous hollow fiber membrane for gas exchange having a blood contact part that contacts blood on one side thereof and a gas contact part that contacts a gas on the other side thereof; and a housing that contains the hollow fiber membranes therein, wherein at least a portion of the blood contact part of the hollow fiber membrane oxygenator is coated with a polymer comprising a repeating unit represented by the following general formula (1) as a main structural component and having a viscosity at 65° C. of 5,000 poise (500 Pa·s).

[Chemical Formula 3]

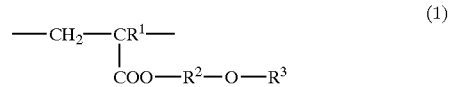

(Wherein $R^1$ is hydrogen or a methyl group, $R^2$ is an alkylene group having 1 to 4 carbon atoms, and $R^3$ is an alkyl group having 1 to 4 carbon atoms).

2. An artificial cardiopulmonary circuit system according to claim 1, wherein the polymer of the formula (1) is polymethoxyethyl acrylate (i.e., in the formula (1), $R^1$ is hydrogen, $R^2$ is an ethylene group, and $R^3$ is a methyl group).

3. An artificial cardiopulmonary circuit system according to claim 1, wherein the polymer has a viscosity of 7,800 poises (780 Pa·s) or more at 65° C.

4. An artificial cardiopulmonary circuit system according to claim 2, wherein the polymer has a viscosity of 7,800 poises (780 Pa·s) or more at 65° C.

5. An artificial cardiopulmonary circuit system according to claim 1, wherein the polymer has a covering amount of 0.02 to 0.5 g/m$^2$.

6. An artificial cardiopulmonary circuit system according to claim 2, wherein the polymer has a covering amount of 0.02 to 0.5 g/m$^2$.

7. An artificial cardiopulmonary circuit system according to claim 3, wherein the polymer has a covering amount of 0.02 to 0.5 g/m$^2$.

8. An artificial cardiopulmonary circuit system according to claim 4, wherein the polymer has a covering amount of 0.02 to 0.5 g/m$^2$.

* * * * *